(12) United States Patent
Prince

(10) Patent No.: US 10,973,990 B2
(45) Date of Patent: Apr. 13, 2021

(54) PROCESSES FOR UTILIZING SAFETY SYRINGE ASSEMBLIES

(71) Applicant: Ty L. Prince, Knoxville, TN (US)

(72) Inventor: Ty L. Prince, Knoxville, TN (US)

( * ) Notice: Subject to any disclaimer, the term of this patent is extended or adjusted under 35 U.S.C. 154(b) by 0 days.

(21) Appl. No.: 16/983,268

(22) Filed: Aug. 3, 2020

(65) Prior Publication Data
US 2020/0360619 A1    Nov. 19, 2020

Related U.S. Application Data

(63) Continuation-in-part of application No. 16/560,044, filed on Sep. 4, 2019, now Pat. No. 10,765,814.

(60) Provisional application No. 62/727,136, filed on Sep. 5, 2018.

(51) Int. Cl.
*A61M 5/32* (2006.01)
*A61B 5/00* (2006.01)

(52) U.S. Cl.
CPC .......... *A61M 5/321* (2013.01); *A61M 5/3204* (2013.01); *A61M 5/3286* (2013.01); *A61M 5/3293* (2013.01); *A61B 5/411* (2013.01); *A61M 2205/584* (2013.01); *A61M 2205/585* (2013.01)

(58) Field of Classification Search
CPC .............. A61M 5/3202; A61M 5/3219; A61M 5/3245; A61M 2005/3217; A61M 2005/2496; A61M 2005/3125; A61M 2005/3246; A61M 2005/3247; A61M 2005/3253; A61M 25/0097; A61M 25/0606

See application file for complete search history.

(56) References Cited

U.S. PATENT DOCUMENTS

| | | | | |
|---|---|---|---|---|
| 3,863,631 A * | 2/1975 | Baldwin | ............... | A61M 25/02 604/513 |
| 5,100,387 A | 3/1992 | Ng | | |
| 5,190,521 A * | 3/1993 | Hubbard | ............... | A61M 5/422 604/117 |
| 5,836,920 A | 11/1998 | Robertson | | |
| 6,190,361 B1 | 2/2001 | Gettig et al. | | |
| 6,322,540 B1 | 11/2001 | Grabis et al. | | |
| 6,575,941 B1 * | 6/2003 | Mumford | ............ | A61M 5/3216 604/192 |
| 7,322,963 B2 * | 1/2008 | Goh | ....................... | A61M 5/158 604/165.03 |
| 7,513,887 B2 * | 4/2009 | Halseth | ............... | A61M 5/3232 604/110 |

(Continued)

*Primary Examiner* — Manuel A Mendez
*Assistant Examiner* — Justin L Zamory
(74) *Attorney, Agent, or Firm* — Gerald R. Black

(57) ABSTRACT

The processes for inserting fluid under the skin of a patient using a safety syringe assembly include initially locating an up-alignment marker. The marker is aligned with a bevel in the needle of the safety syringe assembly so the orientation of the needle bevel is always known by the medical professional, even when the needle bevel cannot be seen. The needle is inserted bevel up prior to insertion. Once inserted, the medical professional inverts the safety syringe assembly so that the bevel is down. This is done by merely flicking the wrist of the hand holding the safety syringe assembly. This prevents splash back of any body fluids from the patient to the medical professional. The same safety syringe assembly and the same process are used for withdrawing fluids from the body of the patient.

15 Claims, 18 Drawing Sheets

Shipping Position

Insertion Position

(56) References Cited

U.S. PATENT DOCUMENTS

| | | |
|---|---|---|
| 9,078,978 B2 | 7/2015 | Schrage |
| 2003/0153874 A1 | 8/2003 | Tal |
| 2003/0187406 A1* | 10/2003 | Spofforth ........... A61M 5/31511 604/218 |
| 2005/0101918 A1 | 5/2005 | Chen et al. |
| 2009/0221961 A1* | 9/2009 | Tal .................... A61M 25/0618 604/103.06 |
| 2011/0202035 A1 | 8/2011 | Voellmicke et al. |
| 2017/0106149 A1 | 4/2017 | Clawson |

\* cited by examiner

Shipping Position

Insertion Position

Disposal Position

INSERT NEEDLE UNDER SKIN TO PROPER DEPTH

INJECTING FLUID INTO THE BODY OF THE PATIENT

INSERT NEEDLE UNDER SKIN TO PROPER DEPTH

WITHDRAWING FLUID FROM BODY OF PATIENT

INSERT NEEDLE UNDER SKIN TO PROPER DEPTH

INJECTING FLUID INTO BODY OF PATIENT

INSERT NEEDLE UNDER SKIN TO PROPER DEPTH

WITHDRAWING FLUID FROM BODY OF PATIENT

Safety Cover with Breakaway Cap

Needle Hub Assembly - Front

Needle Hub Assembly - Rear

Section B-B

Hub Flex Unit

Section A-A

Needle Hub Assembly - Front

Detail "A"
Enlarged View of Needle in Horizontal Position

Needle Hub Assembly - Rear

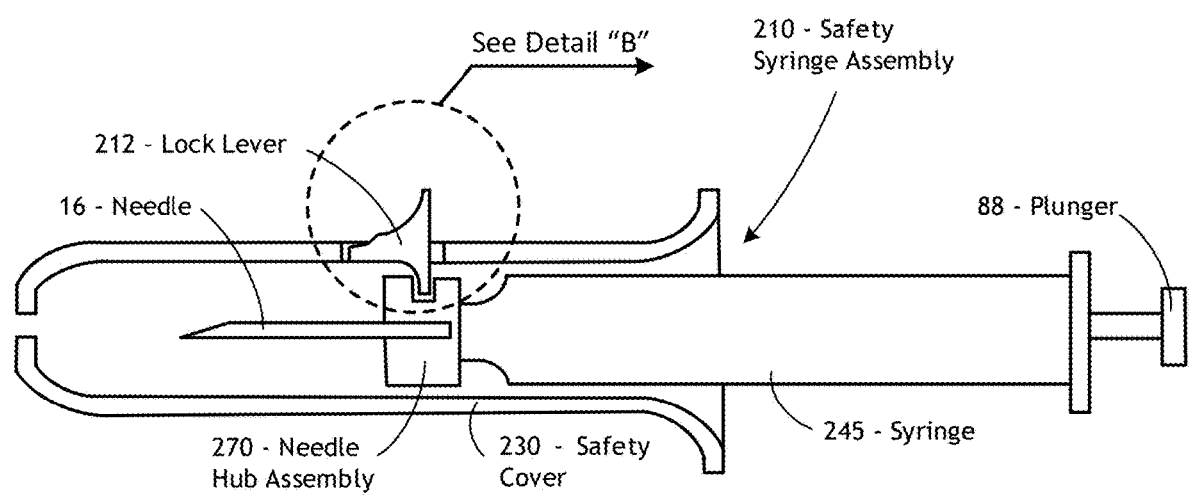
FIGURE 15
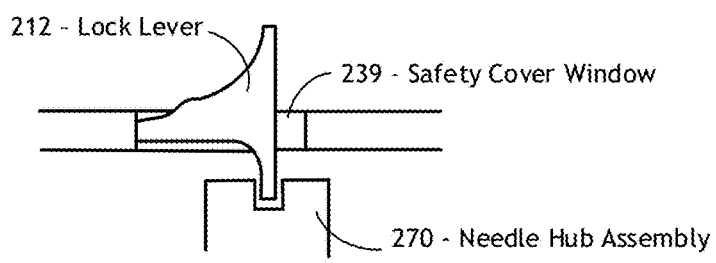
Detail "B"

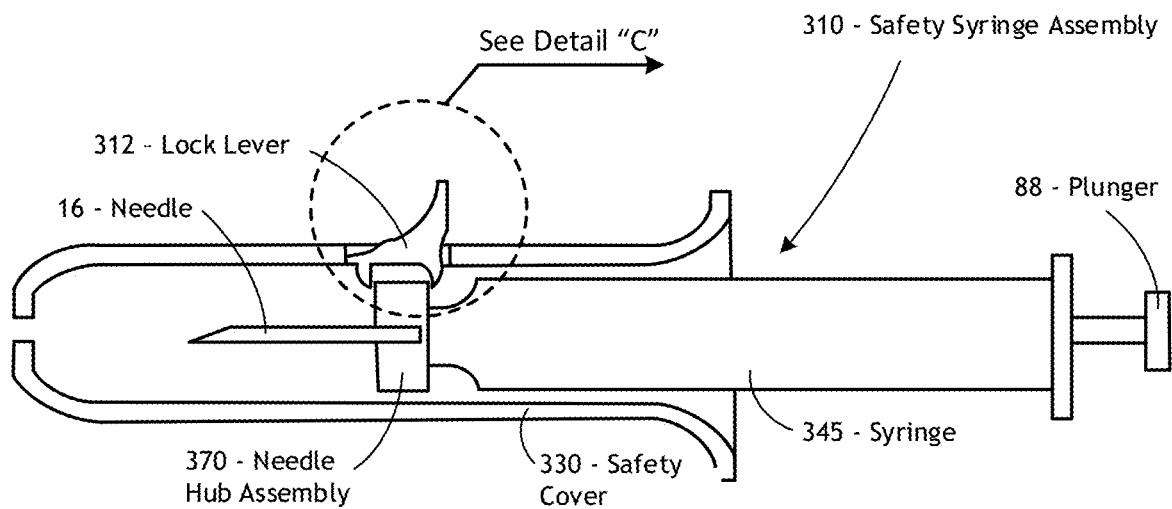
FIGURE 16
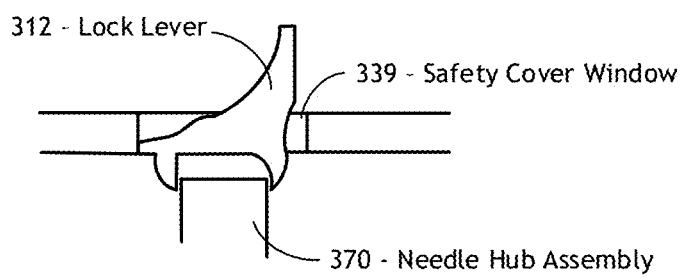
Detail "C"

PROCESSES FOR UTILIZING SAFETY SYRINGE ASSEMBLIES

CROSS-REFERENCE TO RELATED APPLICATIONS

This application is a Continuation-In-Part and claims priority to U.S. patent application Ser. No. 16/560,044, entitled "Safety Syringe Assembly" (Prince) filed on Sep. 4, 2019, which is a Continuation-In-Part and claims priority to U.S. Provisional Application No. 62/727,136, entitled "Safety Syringe Assembly" (Prince) filed on Sep. 5, 2018.

FIELD OF THE INVENTION

This invention relates generally to processes using medical protective devices and more particularly, to methods for injecting and withdrawing fluids using safety syringe assemblies that provide one-handed operation and achieve needle protection for medical personnel while minimizing patient pain and discomfort.

BACKGROUND OF THE INVENTION

Many medical conditions require treatment that include medication administered through injections. Injections may be administered on a regular schedule, and patients needing regular injections often inject the medication themselves or by a family member. Also, accidental stabs from handling syringes and needles are a common problem and can result in transmission of serious diseases.

Conventional syringes may cause problems in inserting a needle at the correct location and minimizing the amount of pain caused.

Beveled needle tips are often used to ease the pain associated with inserting the needle into the skin. Also, the sharply pointed bevel enables a user to accurately target an injection site.

Efforts to properly orientate the bevel of the needle have been made for several decades. Some representative efforts include:

U.S. Patent Document No. 20170156983 (Tennican) discloses a syringe device for mixing and administering a medicant. The system includes a medicant vial; a syringe assembly comprising a barrel and a piston; a protective material supporting the syringe assembly and medicant vial; and a member within the system, the member separating the piston of the syringe assembly from the medicant vial. Systems are provided that can include a syringe assembly comprising a barrel and a piston having a forward end and an opposing back end, a protective material supporting the syringe assembly, and a needle housing coupled to the protective material.

U.S. Pat. No. 9,554,736 (Gupta; et al.) discloses a device with integrated allergy testing which provides an allergy detection system for use during catheterization. The allergy detection system is incorporated into specialized syringes, connectors for use with standard syringes, or can be an independent test module designed for the sole purpose of allergy detection. The detection system features a test strip, and a structure to couple the system to a connector, syringe or a housing, to form an independent test module. The detection system is used to detect potential allergic reactions.

U.S. Pat. No. 4,436,479 (Belloli) discloses a device is described for orienting intravenous needles or other similar articles having relatively long shank portions which terminates in beveled or flat tips. The device has a fixture for supporting the needles at an angle to the horizontal and with the beveled tip resting on a knife edge. A vibrator is coupled to the needle supporting fixture causing the needle to turn to its most stable position on the knife edge where the flat portion engages the knife edge.

There is a need for methods for using safety syringe assemblies to optimize patient comfort, while minimizing any health risks to medical professionals using the syringes.

There is a need for syringe systems that facilitate orientation of the needle bevel to give accurate injections and reduce patient pain.

Although there have been some improvements, there is a need for simple, straight-forward, reliable, easily fabricated devices and methods for using these devices that protect medical personnel and improve patient comfort.

SUMMARY OF THE INVENTION

The processes of the present invention for utilizing the safety syringe assemblies described herein addresses these needs and these objectives.

The safety syringe assembly is for inserting a needle into a patient and injecting fluids into the body of the patient or for withdrawing bodily fluids from the patient.

In a first preferred embodiment, the safety syringe assembly comprises a needle hub assembly and a safety cover. The needle hub assembly includes a needle, a needle hub, and a hub flex unit. The needle is mounted on the front side of the needle hub. A syringe is attachable to the rear side of the needle hub.

The hub flex unit is mounted upon the needle hub and includes a flex arm and a flat. The flex arm prevents the needle hub assembly from sliding during shipping and the flat prevents the needle hub assembly from rotating within in the syringe cover during shipping.

The processes of the present invention for inserting fluid under the skin of a patient using a safety syringe assembly include initially locating a syringe orientation member, such as a red color, on the syringe. The opposite side of the safety cover may have a green color. In this example, red indicates that the needle bevel is up and ready for insertion under the skin of the patient and the green indicates that the needle bevel is down and ready for either dispensing of the fluid into the body of the patient or for withdrawing of bodily fluid from the body of the patient. The up alignment marker is aligned with a bevel in the needle of the safety syringe assembly so the orientation of the needle bevel is always known by the medical professional using the safety syringe assembly, even when the needle bevel itself is under the skin of the patient and cannot be seen.

The needle is inserted bevel up. Once inserted, the medical professional inverts the safety syringe assembly so that the bevel is down. This is done by merely flicking the wrist of the hand holding the safety syringe assembly. This prevents splash back of any bodily fluids from the patient to the medical professional.

The same safety syringe assembly and the same process can also be used for withdrawing fluids from the body of the patient. One preferred embodiment of the safety syringe assembly has an indexing flat to assist in determining how deep to insert the needle, and an indexing ramp which may be useful in determining the angle for injection or removal of fluid.

Proper intra dermal allergy testing requires that the needle bevel be inserted bevel up under the skin of the patient and then rotated bevel down, so that a precise amount is injected and at the same depth for each individual test. This prevents false positives and false negative results because a positive test is defined as an increase in size of 3 MM or greater compared to a saline wheal (which is the negative control test).

In addition, injecting with the bevel down minimizes the likelihood of any back splash, which occurs when someone injects the needle bevel up and does not insert the needle bevel all the way under the skin.

The safety cover secures the needle hub assembly in a first position during shipping. The safety cover secures the needle hub assembly in a second position during insertion of the needle into the patient. The safety cover secures the needle hub assembly in a third position after the needle has been withdrawn from the patient while awaiting disposal. A portion of the safety cover includes magnification enabling a user to view a dosage calibration scale, orient the needle bevel and detect any air bubbles.

The hub flex unit in the safety syringe assembly assumes a first enlarged position during shipping, is compressed during insertion into the patient, and slides back into a third position after usage while awaiting disposal.

In a second preferred embodiment, the safety syringe assembly comprises a needle hub assembly and a safety cover. The needle hub assembly includes a needle, a needle hub, and a conventional hub assembly. The needle is mounted on the front side of the needle hub. A syringe is attachable to the rear side of the needle hub.

As used herein, "orientation alignment marking" refers to some type of color coding or some type of physical structure. A coloring or shading of the magnifier is included in this group.

As used herein, "pointed upward" refers to the orientation of the needle bevel prior to insertion into the body of the patient. Pointed upward means that a person positioned over the needle can see the needle bevel.

As used herein, "pointed downward" refers to the orientation of the needle bevel when fully inserted into the patient. The needle bevel position is such that any splash back from the syringe remains inside the body of the patient and will not reach the medical person handling the syringe.

Still other objectives of the processes for utilizing the safety syringe assemblies of the present invention will become apparent to those skilled in this art from the following description wherein there is shown and described in the preferred embodiment of this invention, simply by the way of illustration of the best modes contemplated for carrying out the present disclosure. As will be realized, the present disclosure is capable of different embodiments, and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

FIG. 15 depicts still another preferred embodiment of the safety cover for use with the safety syringe assembly with a lock lever to enable unobstructed movement of the needle hub assembly from the insertion position to the disposal position. Detail "B" is an exploded view of the lock lever.

FIG. 16 depicts yet still another preferred embodiment of the safety cover for use with the a safety syringe assembly including a lock lever to enable unobstructed movement of the needle hub assembly from the insertion position to the disposal position along with a Detail "C" of the lock lever.

DETAILED DESCRIPTION OF THE PRESENT INVENTION

Figure 1A:
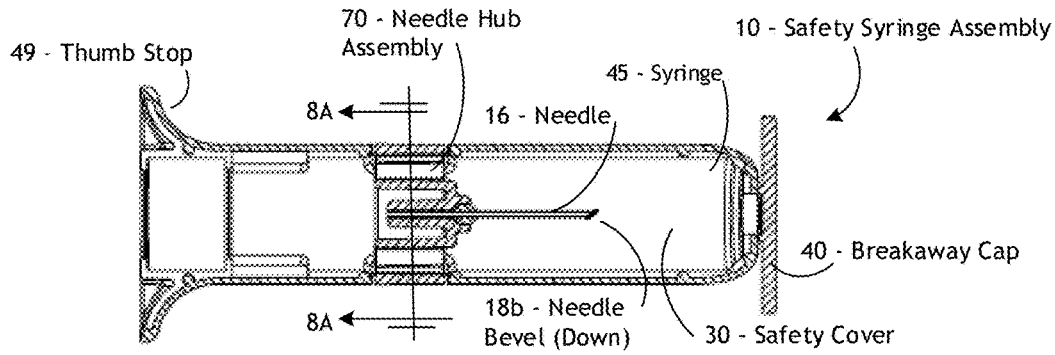
FIG. 1A depicts a side elevational view of a first preferred embodiment of a safety syringe assembly for use in processes for utilizing the safety syringe assemblies of the present invention, with a needle hub assembly in a shipping position.
Figure 1B:
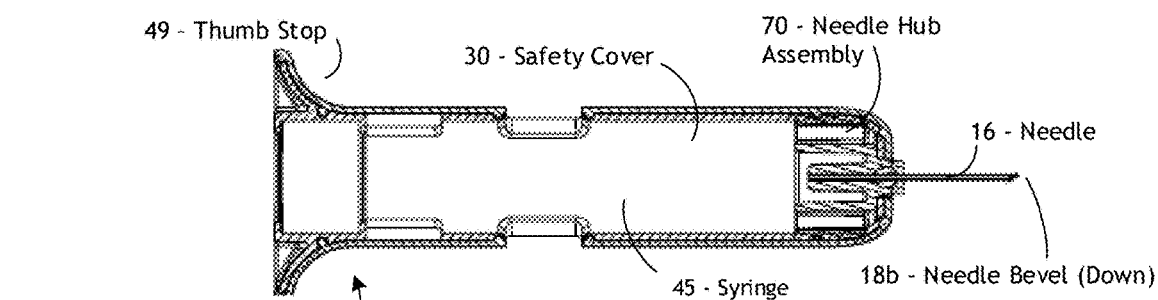
FIG. 1B depicts a side elevational view of the safety syringe assembly of FIG. 1A, with a needle hub assembly in an insertion position for inserting the needle into the skin of the patient.
Figure 1C:
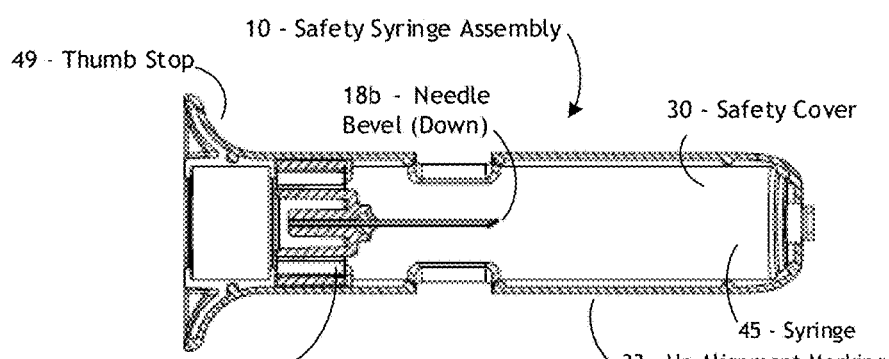
FIG. 1C depicts a side elevational view of the safety syringe assembly of FIG. 1A, with a needle hub assembly, the safety syringe assembly having been used and being in a disposal position.

Referring now to the drawings, FIGS. 1A, 1B, and 1C each depict side elevational views of a third preferred embodiment of a safety syringe assembly for use with the methods of the present invention [10].

FIGS. 1A and 1B depict side views of a first preferred embodiment of the safety syringe assembly [10] for use in the processes of the present invention, FIG. 1A being the safety syringe assembly prior to insertion under the skin of the patient, and FIG. 1B being the safety syringe assembly after insertion under the skin of the patient and injecting fluid into the body of the patient.

The safety syringe assembly for use with the processes of the present invention [10] preferably comprises a needle hub assembly [70] and a safety cover [30].

FIG. 1A depicts the safety cover [30] housing the needle hub assembly [70] in a first position for shipping. FIG. 1B depicts the safety cover [30] housing the needle hub assembly [70] in a second position for insertion of the needle [16] into the skin of the patient. FIG. 1C depicts the safety cover [30] housing the needle hub assembly [70] in a third position, the safety syringe assembly [10] having been used and awaiting disposal.

The needle hub assembly [70] includes a hub flex unit [74] mounted upon a needle hub [76], and the needle hub [76] for retaining the needle [16] securely mounted therewithin. The hub flex unit [74] includes a flex arm [77] and a flat [78]. The flex arm [77] prevents the needle hub assembly [70] from sliding within the safety cover [30] during shipping. The flat [78] prevents the needle hub assembly [70] from rotating within the safety cover [30] during shipping.

The needle hub assembly [70] is preferably color coded at the factory, for either a long injection needle (for example, blue) or a shorter needle for testing (for example, white). This ensures that the proper needle length is used for either injection or testing. The current needles used in the industry color code the cap. The cap is a separate piece which can be switched. If the color-coded caps are switched, a longer injection needle may be used for testing and a shorter testing needle may be used for injections. Using the incorrect needle length can give false allergy test results or not enable the allergy fluid to be injected to the proper depth under the skin.

In addition, the safety cover [30] preferably uses visual indicators or alignment markers [33 and 34], such as colored stripes (for example, a green and a red stripe on the safety cover [30]) to indicate the orientation of the needle bevel [18]. In this example, red shows bevel [18] up for insertion under the skin and the green shows the needle bevel [18] down for dispensing of the fluid under the skin.

The safety cover [30] is preferably made of clear material enabling light to enter the safety cover [30] providing for a clear view of the needle bevel [18] orientation, the needle length, as well as enabling light into the safety cover [30] for the reading of the syringe volume scale [46], through the lens, during the process of filling the syringe [45] from the vial of allergy fluid.

The safety cover [30] preferably protects either a short needle [16] for testing or a longer needle [16] for injections. The safety cover [30] includes a window [39].

The safety syringe assembly for use with the processes of the present invention [10] enables one-handed operation by the medical technician or user.

The safety cover [30] and needle hub assembly [70] for use with the processes of the present invention are both indexed to the needle bevel ensuring that during either testing or injection, the needle [16] is bevel up [18a] for insertion and bevel down [18b] for dispensing. The current needle used in the allergy industry is not indexed to the needle bevel. This enables the needle bevel to be inserted in any orientation and dispensed in any orientation. This current product is deficient in that it does not enable the proper circular bubble to be created under the skin for testing (enabling false positives or no positive at all) and can cause the fluid to be sprayed back onto the medical technician or user during injection.

The safety cover [30] has now moved past the original position with the needle hub pads locked into recesses into this safe (disposal) pocket of the safety cover [30]. Once in this position, the needle [16], needle hub [76], safety cover [30] and syringe [45] can be disposed of together or the needle [16], needle hub [76] and safety cover [30] can be removed from the syringe [45] and disposed of separately.

Figure 2A:
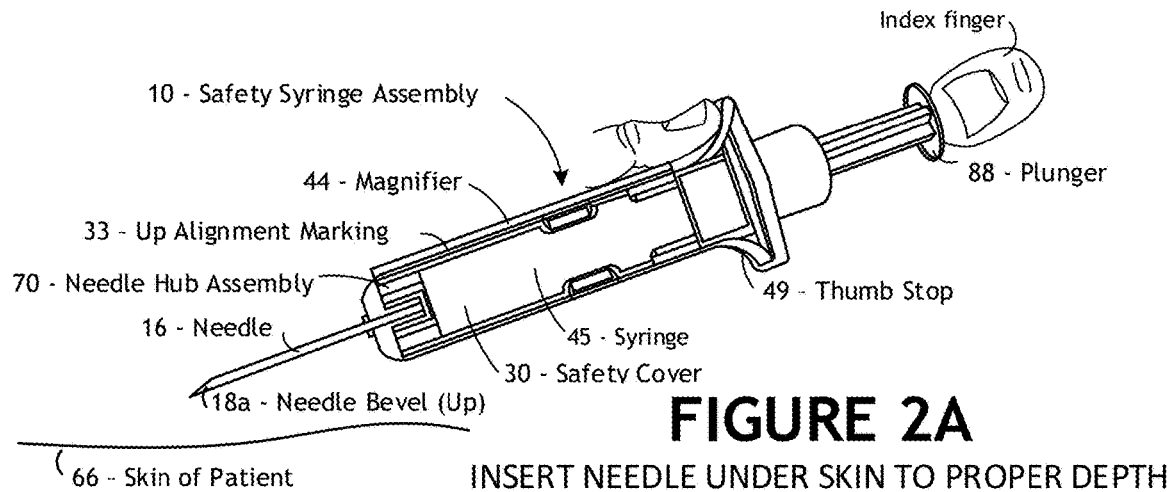
FIGS. 2A and 2B depict side views of the first preferred embodiment of the process for using a safety syringe assembly of the present invention depicted in FIGS. 1A, 1B, and 1C, FIG. 2A being the safety syringe assembly prior to insertion under the skin of the patient, and FIG. 2B being the safety syringe assembly after insertion under the skin of the patient and injecting fluid into the body of the patient.
Figure 2B:
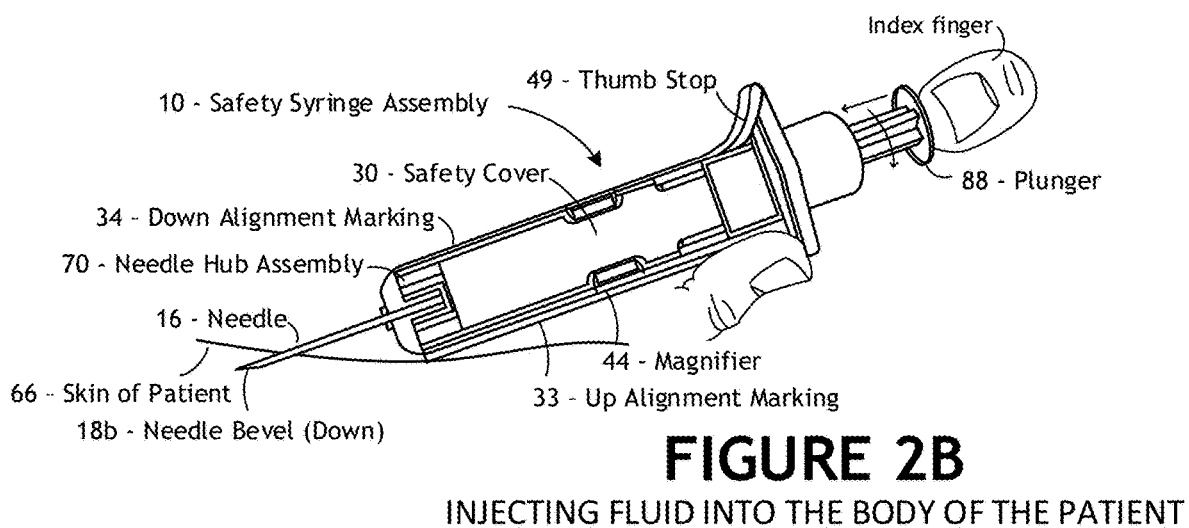

FIGS. 2A and 2B depict side views of a second preferred embodiment of the process for using a safety syringe assembly of the present invention, FIG. 2A being the safety syringe assembly prior to insertion under the skin of the patient, and FIG. 2B being the safety syringe assembly after insertion under the skin of the patient and injecting fluid into the body of the patient.

Figure 3A:
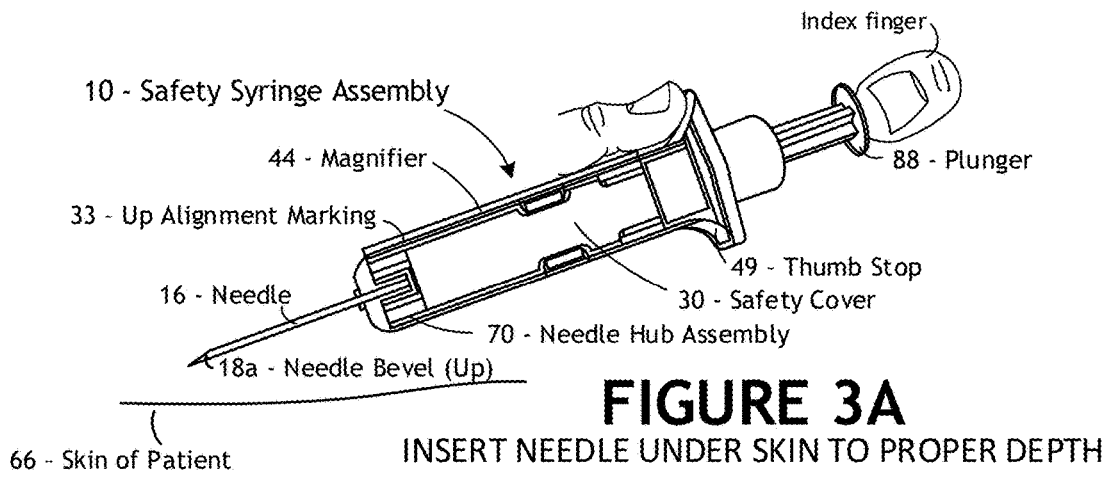
FIGS. 3A and 3B depict side views of a first preferred embodiment of the process for using a safety syringe assembly of the present invention depicted in FIGS. 1A, 1B, and 1C, FIG. 3A being the safety syringe assembly prior to insertion under the skin of the patient, and FIG. 3B being the safety syringe assembly after insertion under the skin of the patient and withdrawing bodily fluid from the patient.
Figure 3B:
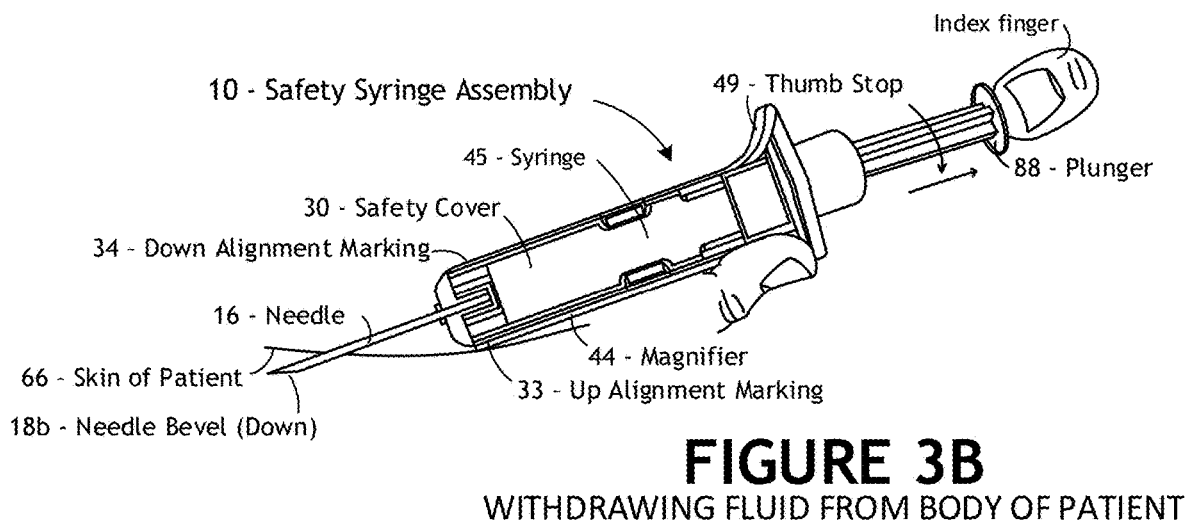

FIGS. 3A and 3B depict side views of the first preferred embodiment of the process for using a safety syringe assembly of the present invention, FIG. 3A being the safety syringe assembly prior to insertion under the skin of the patient, and FIG. 3B being the safety syringe assembly after insertion under the skin of the patient and withdrawing bodily fluid from the patient.

Figure 4A:
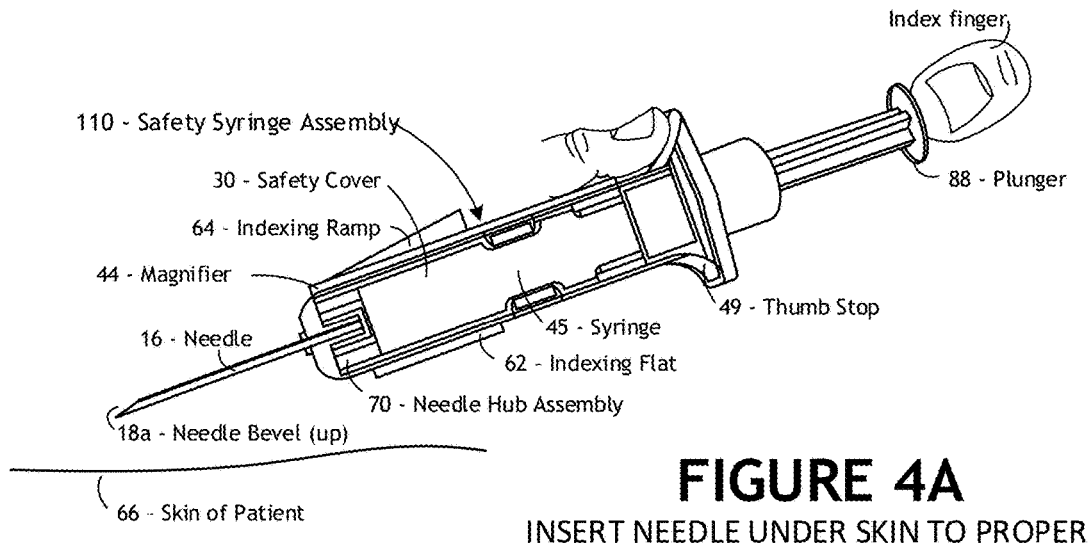
FIGS. 4A and 4B depict side views of a second preferred embodiment of the process for using a safety syringe assembly of the present invention, FIG. 4A being the safety syringe assembly prior to insertion under the skin of the patient, and FIG. 4B being the safety syringe assembly after insertion under the skin of the patient and injecting fluid into the body of the patient.
Figure 4B:
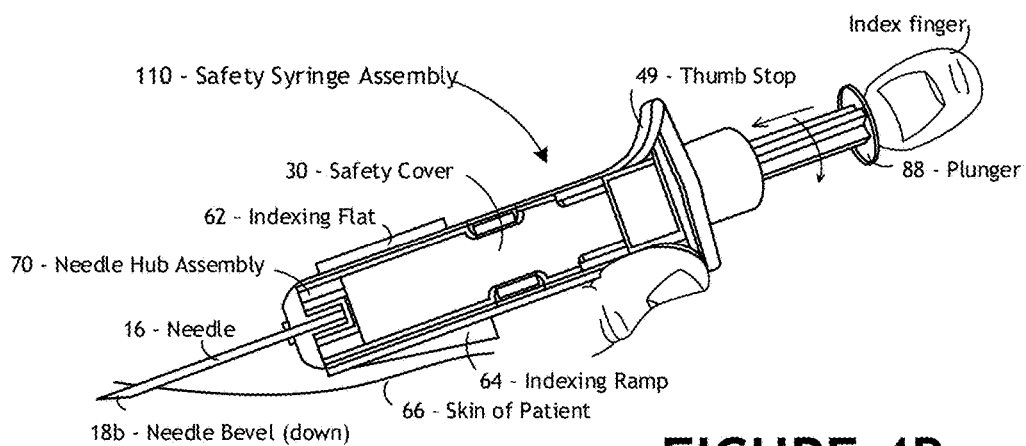

FIGS. 4A and 4B depict side views of the second preferred embodiment of the process for using a safety syringe assembly of the present invention, FIG. 4A being the safety syringe assembly prior to insertion under the skin of the patient, and FIG. 4B being the safety syringe assembly after insertion under the skin of the patient and withdrawing bodily fluid from the patient.

Figure 5A:
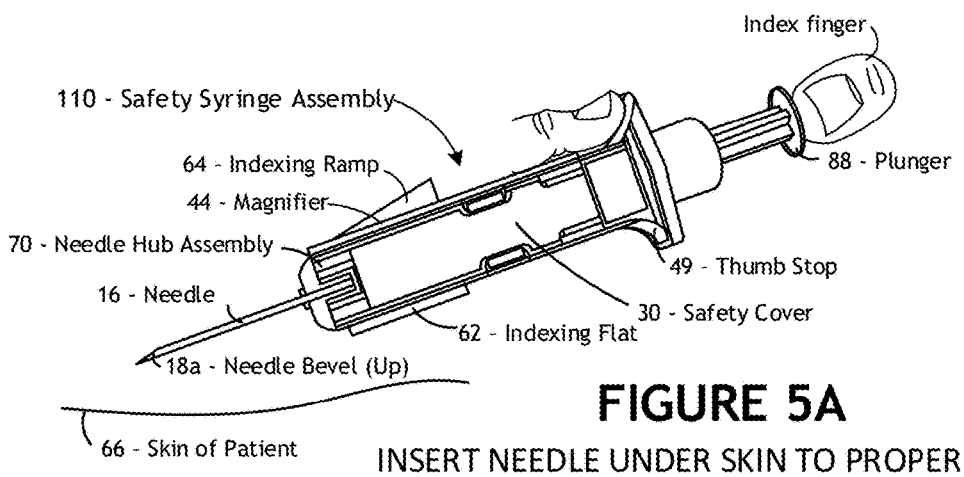
FIGS. 5A and 5B depict side views of the second preferred embodiment of the process for using a safety syringe assembly of the present invention, FIG. 5A being the safety syringe assembly prior to insertion under the skin of the patient, and FIG. 5B being the safety syringe assembly after insertion under the skin of the patient and withdrawing bodily fluid from the patient.
Figure 5B:
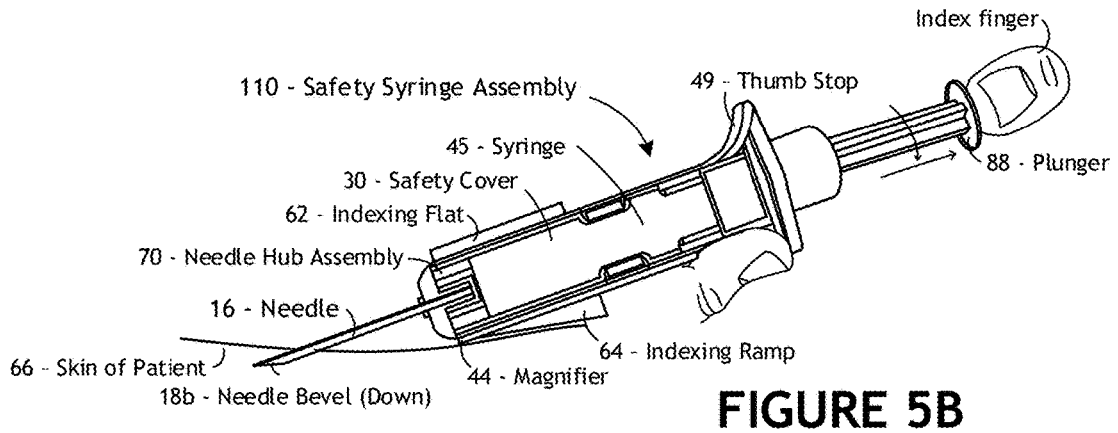

FIGS. 5A and 5B depict side views of the second preferred embodiment of the process for using a safety syringe assembly of the present invention, FIG. 5A being the safety syringe assembly prior to insertion under the skin of the patient, and FIG. 5B being the safety syringe assembly after insertion under the skin of the patient and withdrawing bodily fluid from the patient.

The processes of the present invention for inserting fluid under the skin of a patient using a safety syringe assembly include initially locating a syringe orientation member, such as a red color, on the syringe. The opposite side of the safety cover may have a green color. In this example, red indicates that the needle bevel is up [18a] and ready for insertion under the skin of the patient [66] and the green indicates that the needle bevel is down [18b] and ready for either dispensing of the fluid into the body of the patient or for withdrawing of bodily fluid from the body of the patient. The up alignment marker [33] is aligned with a bevel in the needle [16] of the safety syringe assembly [10] so the orientation of the needle bevel is always known by the medical professional using the safety syringe assembly [10], even when the needle bevel itself is under the skin of the patient [66] and cannot be seen.

The needle [16] is inserted bevel up [18a]. Once inserted, the medical professional inverts the safety syringe assembly [10] so that the bevel is down [18b]. This is done by merely flicking the wrist of the hand holding the safety syringe assembly [10] and prevents splash back of any bodily fluids from the patient to the medical professional.

The same safety syringe assembly [10] and the same process can also be used for withdrawing fluids from the body of the patient [66]. One preferred embodiment of the safety syringe assembly [110] includes a first needle-injection member or indexing flat [62] to assist in determining how deep to insert the needle [16]. Also, included is a second needle-injection member or an indexing ramp [64] which is useful in determining the angle for inserting the needle [16].

For example, the method of the present invention enables the needle for allergy testing fluid to be injected to a specific depth under the skin of a patient. The safety syringe assembly is guided by an indexing flat [62] projecting from the safety cover [30]. In one preferred embodiment the safety syringe assembly includes an orientation alignment marking so that the medical professional using the safety syringe assembly [10] always knows the position of the needle bevel, even when the needle bevel is under the skin of the patient [66]. The needle [16] is inserted under the skin of the patient with the needle bevel up [18a] to minimize patient discomfort. Once under the skin of the patient [66], the medical professional places the needle bevel down [18b] by rotation of the wrist holding the safety syringe assembly, preferably between an angle of 75 degrees and 285 degrees. This will minimize any splash back during the allergy testing process.

In the first embodiment of the safety syringe assembly [10] depicted in FIGS. 2A, 2B, 3A, and 3B for use with the processes hereof, the safety syringe assembly [10] preferably deploys colors are used to mark the needle bevel up position. One example is to mark the [18a] position red and the [18b] position green. Another embodiment tints the magnifier [44] a color, such as red.

In the second embodiment of the safety syringe assembly [110] depicted in FIGS. 4A, 4B, 5A, and 5B for use with the processes hereof, the safety cover [30] of the safety syringe assembly [110] includes an indexing ramp [64] and an indexing flat [62], each of which are disposed on opposing outer surfaces, preferably 180 degrees apart. Preferably, the alignment ramp is centered relative to the needle bevel. The indexing ramp [64] is used by the medical professional for calibrating needle depth and the indexing flat [62] is used for determining needle angle.

Figure 6:
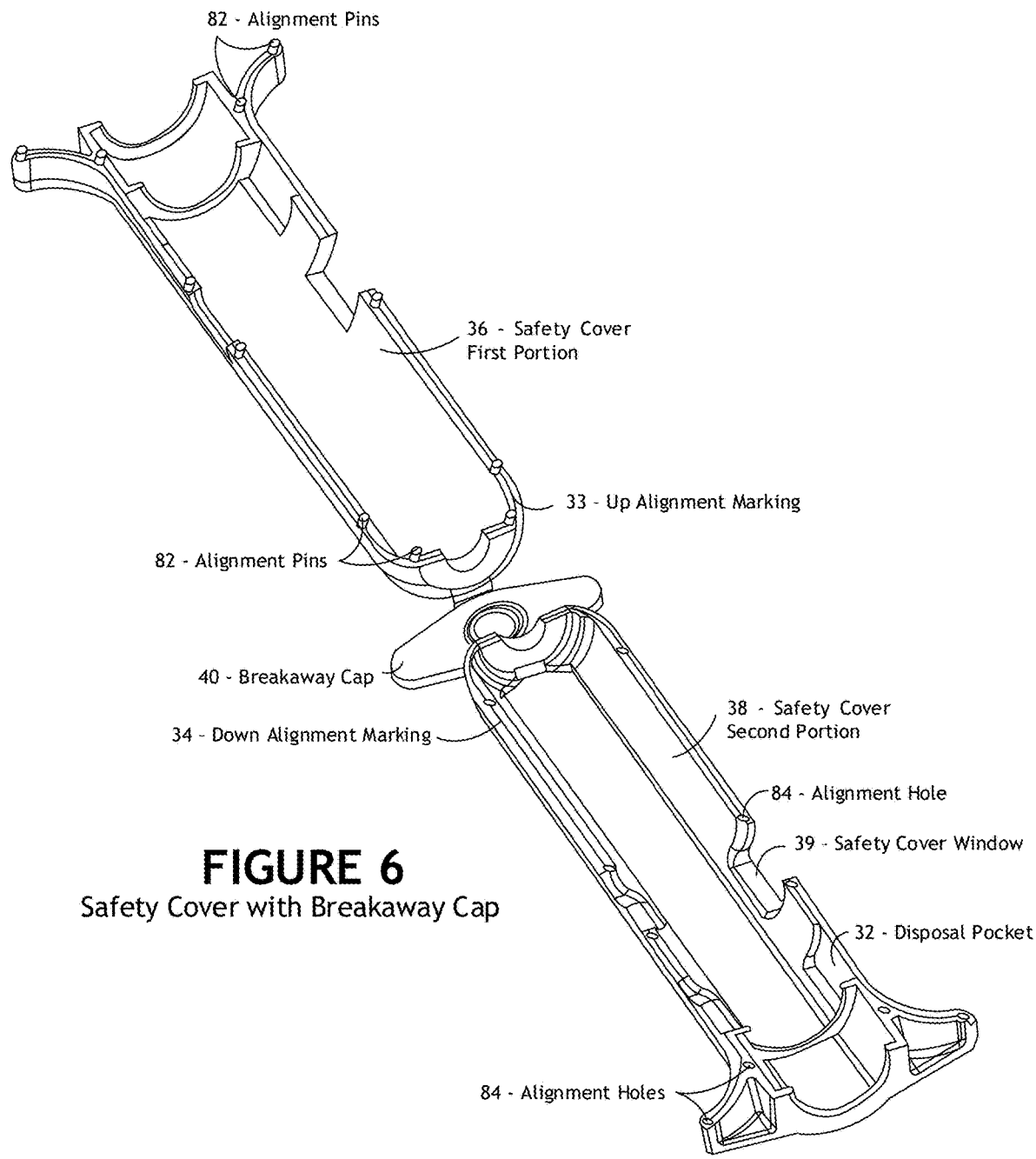
FIG. 6 depicts a side elevational view of the safety cover for use in the safety syringe assembly of FIGS. 1A, 1B, and 1C, the safety cover including two halves joined by a breakaway cap.

FIG. 6 depicts a side elevational view of the safety cover [30] for use in the safety syringe assembly [10] of FIGS. 1A, 1B, and 1C. The safety cover [30] includes two halves joined by a breakaway cap [40]. The breakaway cap [40] is attached to both halves of the safety cover [30], holding them together and in position, relative to each other, until needle hub assembly [70] can be placed into the safety cover [30] and the breakaway cap [40] glued closed. Preferably, the two halves of the safety cover [30] are glued together. The adhesive is applied as recommended by the manufacturer taking care to avoid the hub assembly and the windows [39].

Also depicted are the two openings for the needle hub pads assemblies, an initial position, as well as the locking recesses used to lock the needle hub assembly [70] into a disposal position.

The assembly is closed, clamped and cured per manufacturer instructions. Packaging and sterilization protocols are then followed.

Figure 7A:
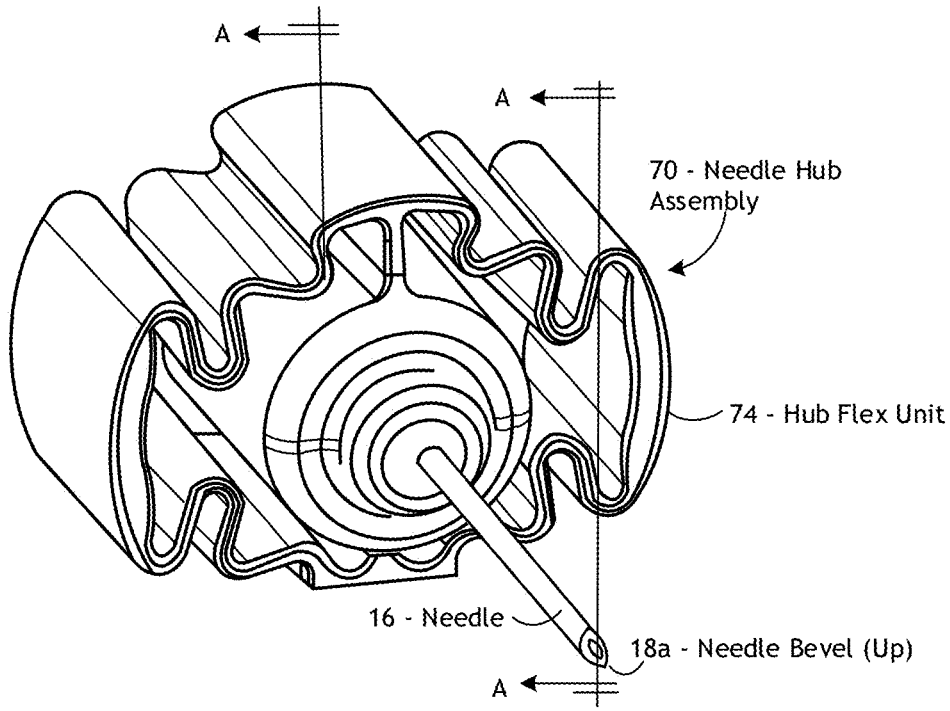
FIG. 7A depicts a front view and FIG. 7B depicts a rear view of the third preferred embodiment of the needle hub assembly of FIGS. 1A, 1B, and 1C, including the needle, a needle hub, and a needle flex unit.
Figure 7B:
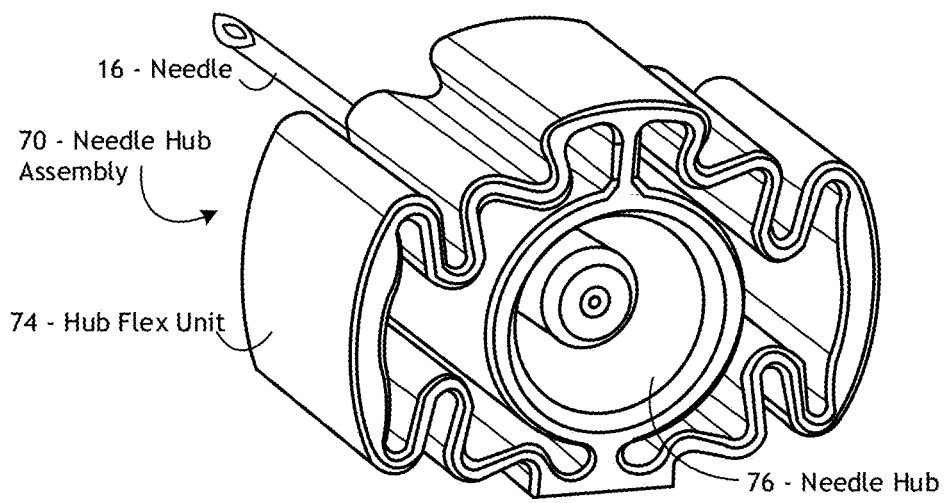

FIG. 7A depicts a front view and FIG. 7B depicts a rear view of a first preferred embodiment of the needle hub assembly [70] of FIGS. 1A, 1B, and 1C, including the needle [16], a needle hub [76], and a needle flex unit [74]. The needle hub [76] includes locking pads and four spring members, two spring members for each pad, that are used to hold the needle [16] and needle hub [76] in an initial position or are used to lock the needle [16] and needle hub [76] in a locked position for disposal.

Figure 8A:
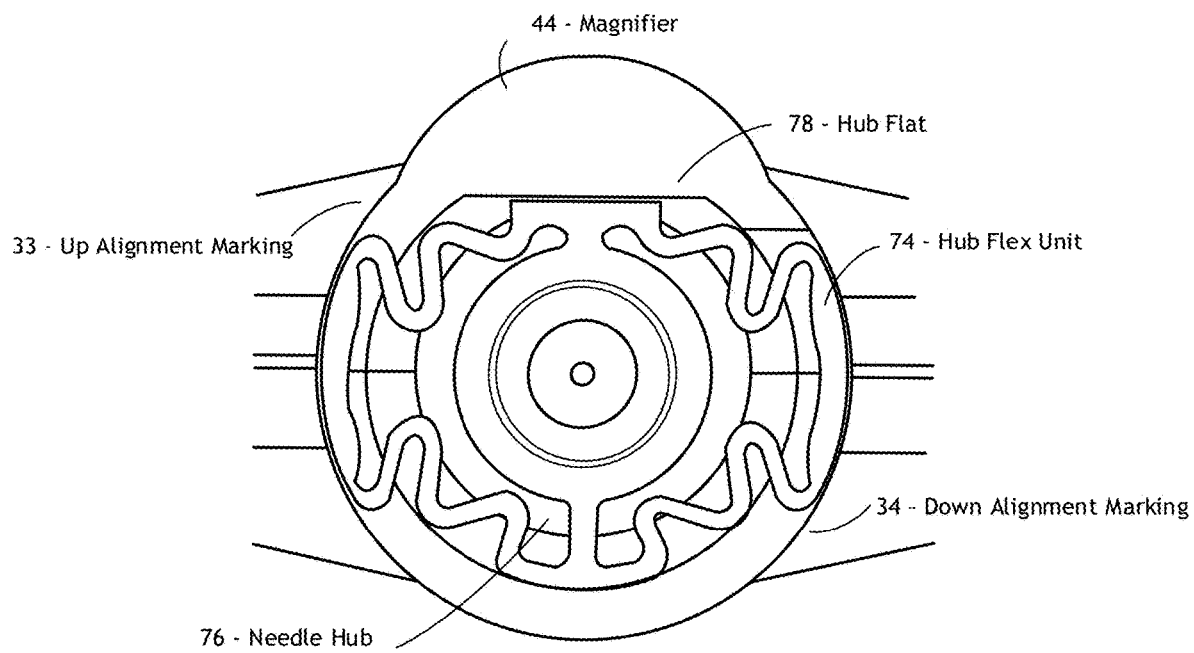
FIG. 8A depicts a cross sectional view through the safety cover and the needle and needle hub. This shows the up-alignment marker (e.g.=a red stripe), on the left, the needle bevel is up toward the up-alignment marker and the down-alignment marker (e.g.—a green stripe) is on the right. Also depicted is the needle hub indexing flat toward the magnifier. This design ensures that the needle is always pointed upward toward the up-alignment marker, is always 90 degrees from the needle hub flat and that the needle, the needle bevel, the needle hub are always indexed, with respect to the safety cover, enabling the needle bevel to be toward the up-alignment marker, when viewed through the magnifier or provides the user knowledge of the orientation of the needle bevel relative to the safety cover.

FIG. 8A depicts a cross sectional view through the safety cover [30] and the needle [16] and needle hub [76]. This shows the red stripe, on the left, the needle is bevel up [18a] toward the red stripe and the green stripe on the right. Also depicted is the needle hub [76] indexing flat [78] toward the magnifier. This design insures that the needle [16] is always pointed upward toward the red stripe, is always 90 degrees from the needle hub flat [78] and that the needle [16], the needle bevel, the needle hub [76] are always indexed, with respect to the safety cover [30], enabling the needle bevel to be toward the red stripe, when viewed through the magnifier or gives the user knowledge of the position of the needle bevel position relative on the safety cover [30]. This shows the red stripe, on the left, the needle is bevel up [18a] toward the red stripe and the green stripe on the right. It also shows the needle hub indexing flat [78] toward the magnifier. This design ensures that the needle [16] is always pointed up toward the red stripe, is always 90 degrees from the needle hub flat [78] and that the needle [16], the needle bevel, the needle hub [76] are always indexed, with respect to the safety cover [30], enabling for the needle bevel to be toward the red stripe, when viewed through the magnifier or provides the medical professional knowledge of the position of the needle bevel relative to the red stripe on the safety cover [30].

Figure 8B:
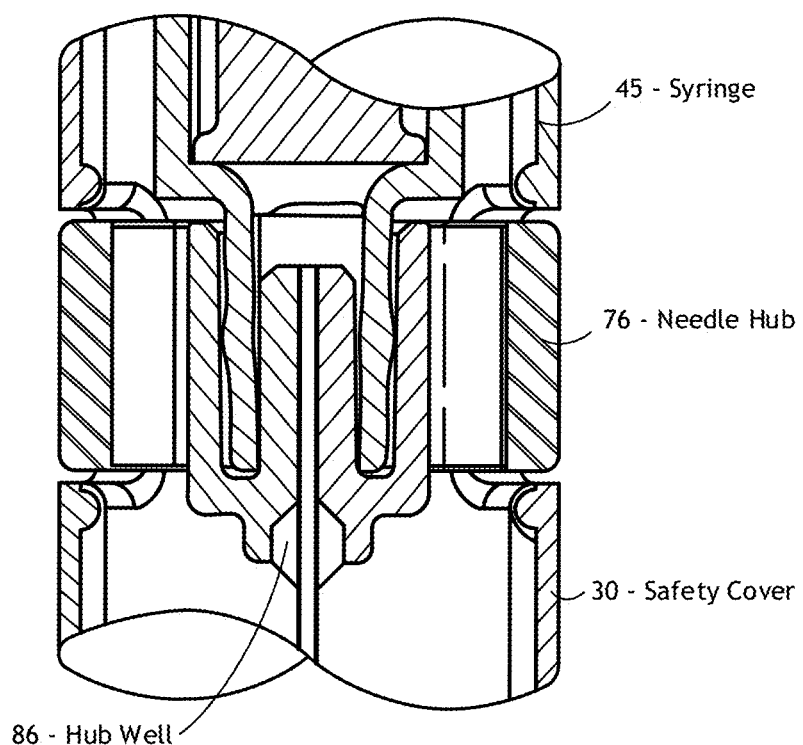
FIG. 8B depicts a cross sectional view through the safety cover, the needle, the needle hub and the syringe of the safety syringe assembly of FIG. 8A. The end of the syringe attaches to the needle hub, with the raised bump ring on the end of the syringe. This shows how the safety syringe assemblies used with the methods of the present invention are compatible with existing syringe designs.

FIG. 8B depicts a cross-sectional view through the safety cover [30], the needle [16], the needle hub [76] and the syringe [45] of the safety syringe assembly [10] of FIG. 12A. The end of the syringe [45] attaches to the needle hub [76], with the raised bump ring on the end of the syringe

[45]. This shows how the safety syringe assembly for use with the processes of the present invention [10] are compatible with existing syringe designs. FIG. 8B depicts how the end of the syringe [45] attaches to the needle hub assembly [70], with the raised bump ring on the end of the syringe [45]. This design enables the safety syringe assembly [10] to be compatible with an existing syringe design. This syringe design is made in the millions each year. Slight modifications to the needle hub [76] can be made enabling the safety syringe assembly [10] to be used with other standard medical syringes.

Figure 9:
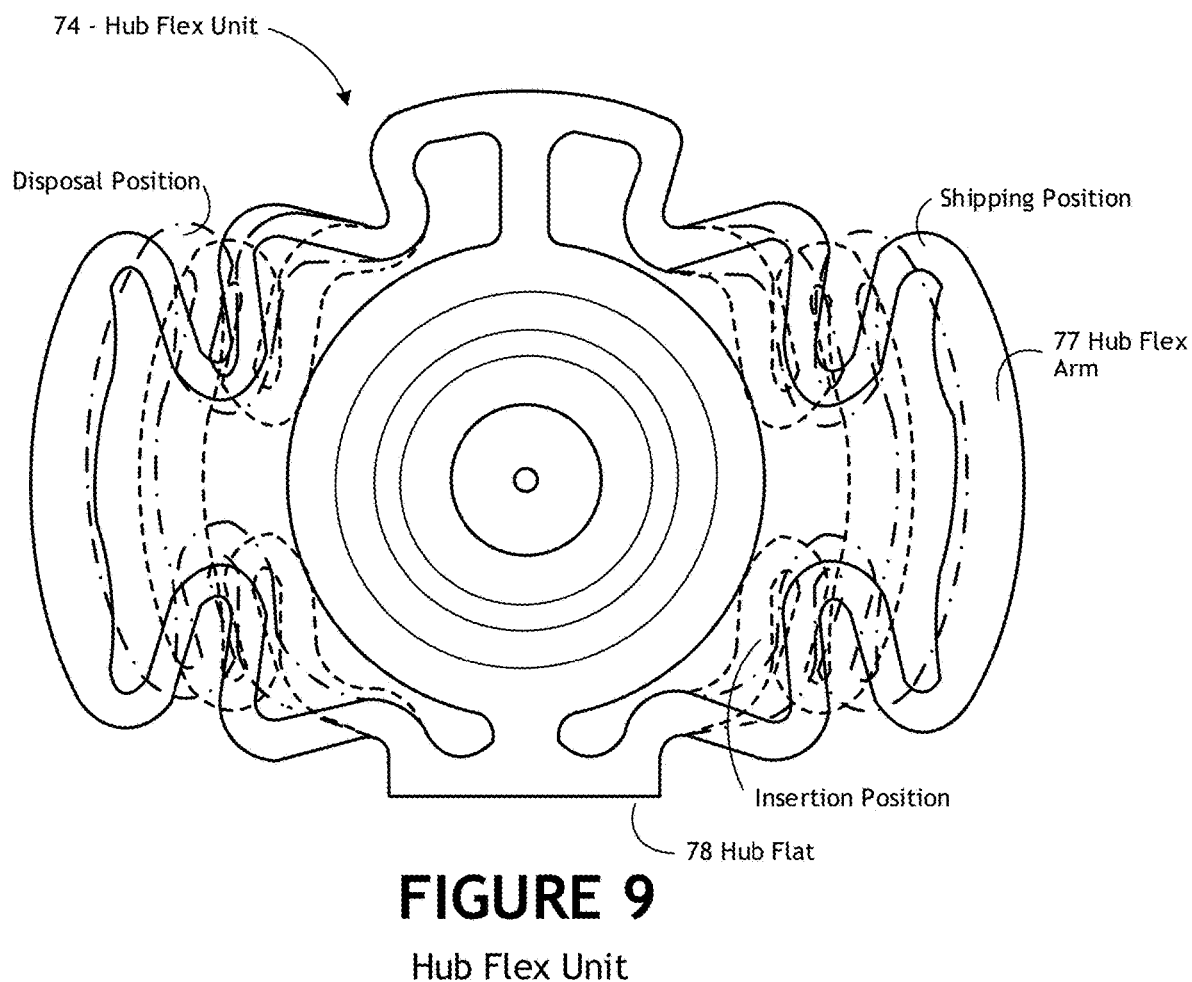
FIG. 9 depicts the hub flex unit of the safety syringe assemble of FIGS. 1A, 1B, and 1C, highlighting the hub flex unit having three distinct positions—the shipping position, the insertion position, and the disposal position.

FIG. 9 depicts the hub flex unit [74] of the safety syringe assembly [10] of FIGS. 1A, 1B, and 1C, highlighting the hub flex unit, the hub flex unit being in a first position during shipping, the hub flex unit being in a second position during insertion of the needle [16] into the skin of the patient [66], and the hub flex unit [74] being in a third position after the needle [16] has been inserted into the skin of the patient awaiting disposal.

The safety syringe assembly [10] for use with the processes of the present invention [10] enables the medical professional to push one or two buttons on the needle hub [76], releasing the needle [16] and hub from an initial safety position. After the release, the syringe [45], protected needle [16] and safety cover [30] can be placed on the top of the vial of allergy fluid and be safely inserted into the vial for the extraction of the fluid into the syringe [45]. This protects the medical technician from the potential stick hazard of an exposed needle [16] during the process of extracting fluid from the vial.

Figure 10:
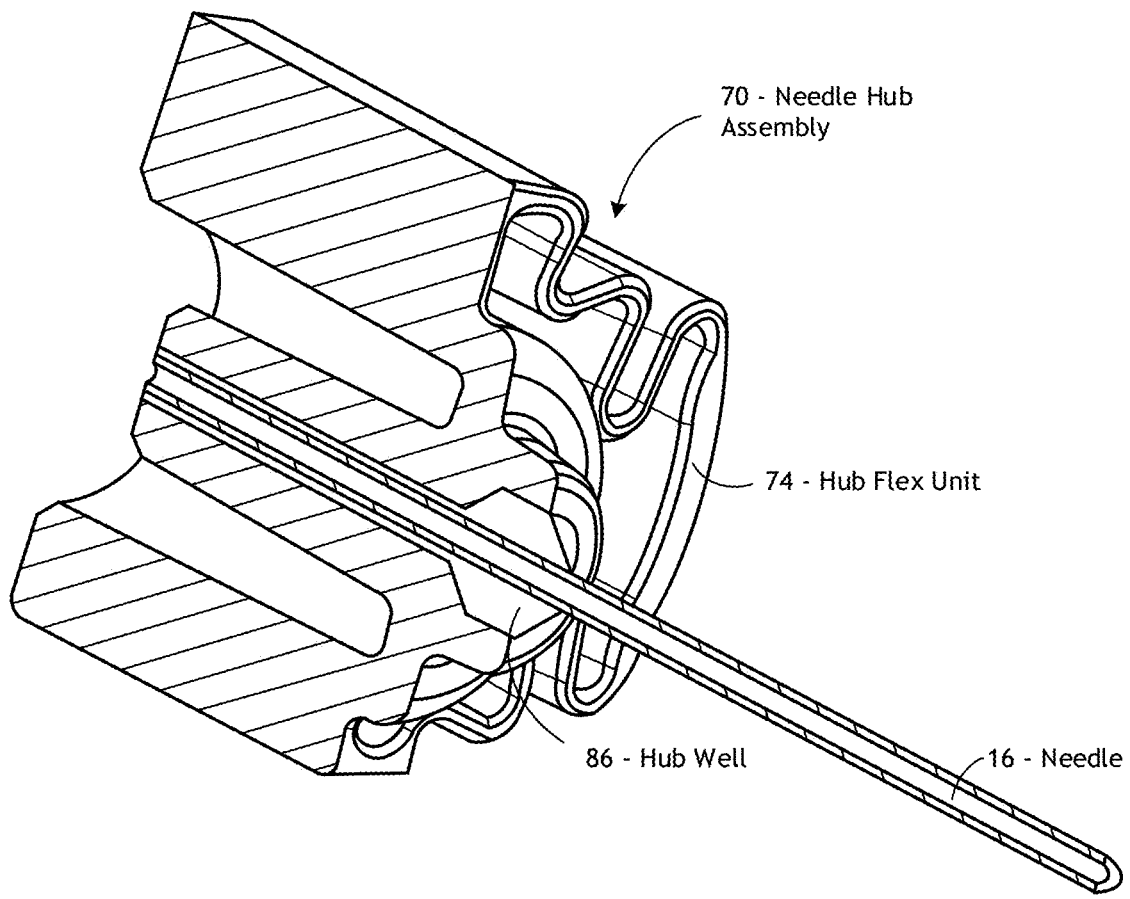
FIG. 10 depicts a half-section of the needle hub assembly taken from FIG. 7A.

FIG. 10 depicts a half-section of the needle hub assembly [70] of FIG. 9A. The hub well, into which the cannula is inserted, has two functions. The hub well [86] helps to align the adhesive-dispensing tip with the cannula-to-hub bond joint and the hub well [86] helps to promote adhesive flow into the bond line.

Figure 11:
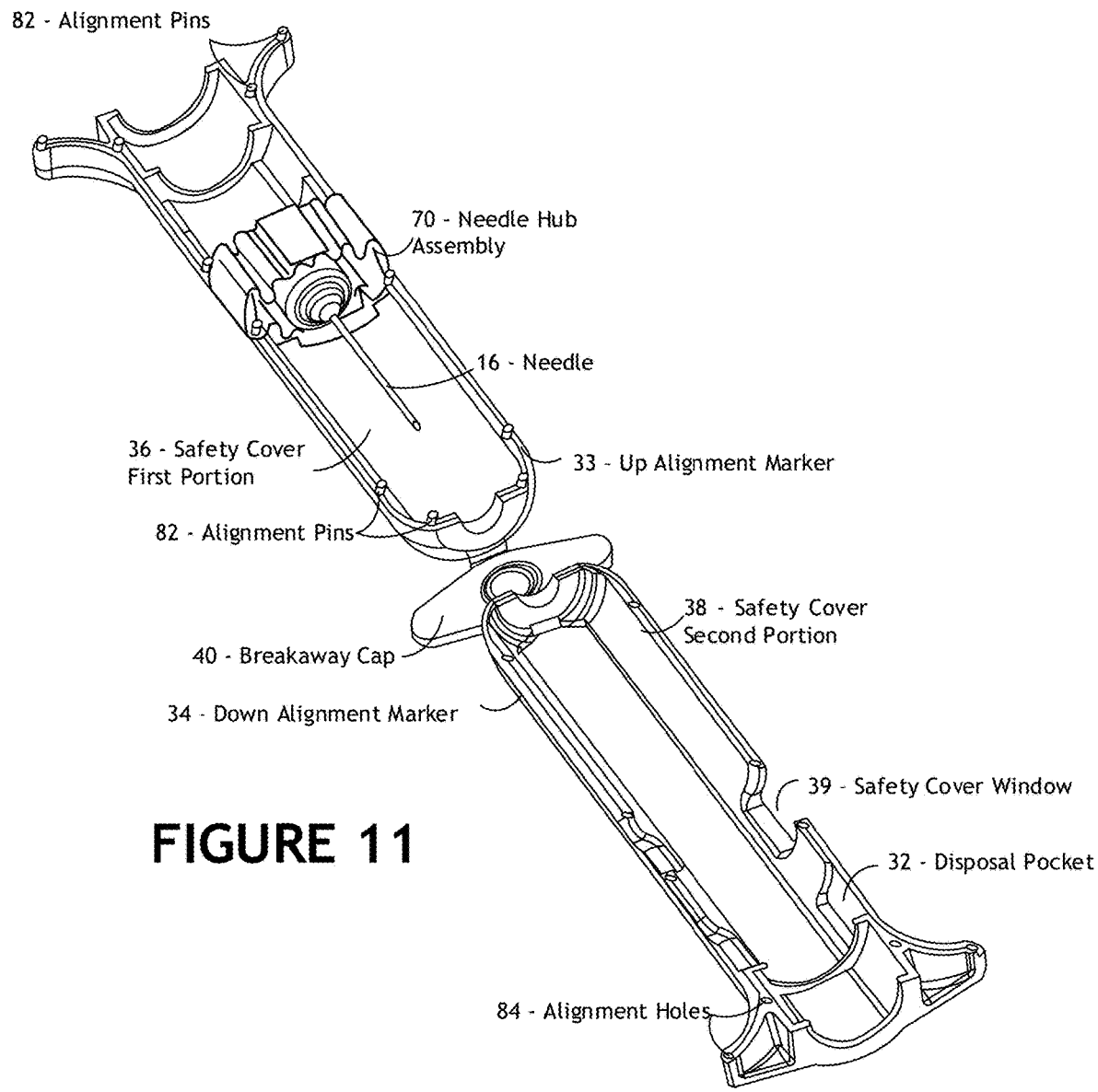
FIG. 11 depicts the needle hub assembly of FIGS. 7A and 7B positioned in one half of the safety cover for use in the safety syringe assembly of FIG. 6, the safety cover including two halves joined by the breakaway cap.

FIG. 11 depicts the needle hub assembly of FIGS. 7A and 7B positioned in one half of the safety cover [30] for use in the safety syringe assembly [10] of FIG. 6, the safety cover [30] including two halves joined together by the breakaway cap [40].

The needle [16] and needle hub [76] are inserted into a half [36] of the safety cover without the magnifier [44]. Also, the needle [16] and needle hub [76] are depicted in their initial position. After the needle [16] and needle hub [76] are placed into this position, an adhesive can be placed on the edge of half of the safety cover [30] and the safety cover [30] is closed, creating the safety cover [30], needle [16] and needle hub assembly [70]. This safety syringe assembly [10] is now ready to have the syringe [45] inserted.

Figure 12:
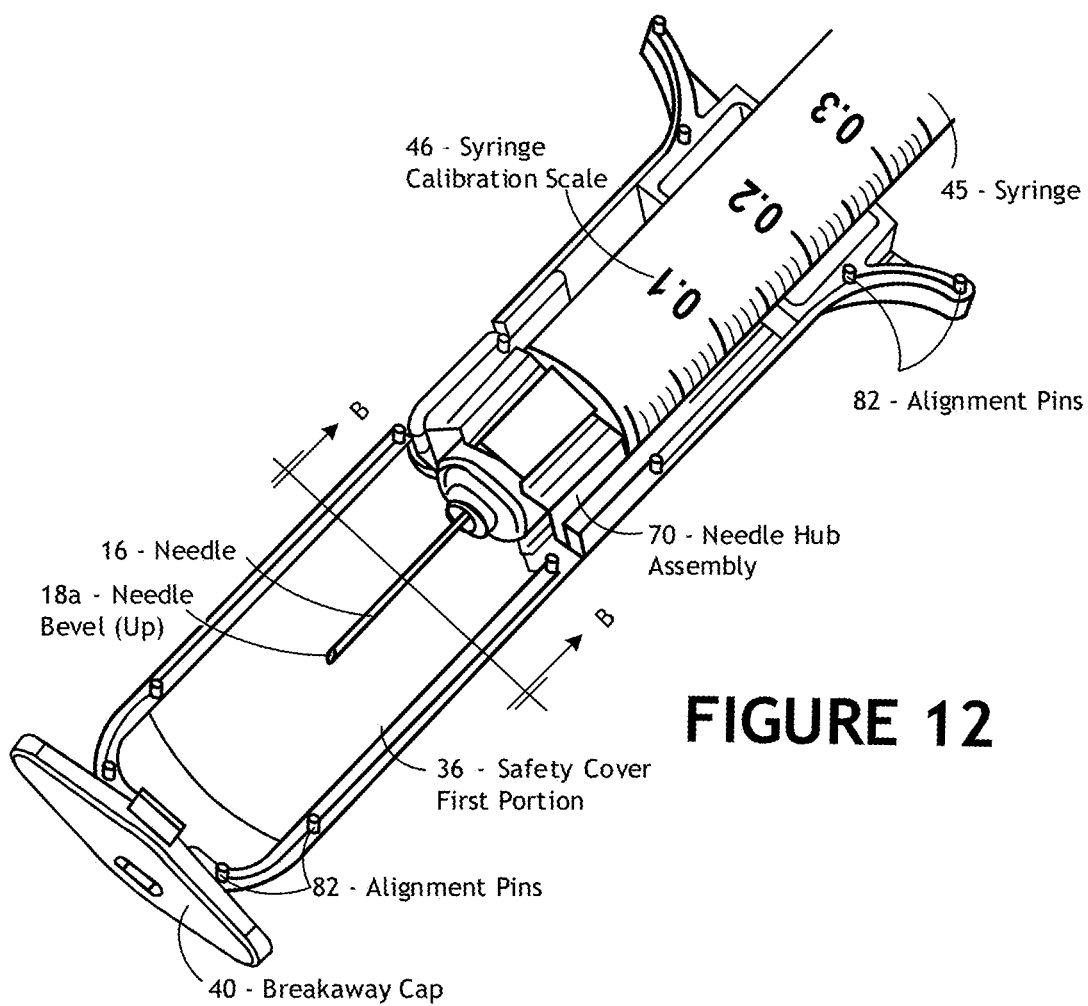
FIG. 12 depicts the beveled needle and needle hub assembly placed into half of the safety cover of FIG. 6, the needle and needle hub assembly, in the first position with the syringe attached to the needle hub assembly.

FIG. 12 depicts the needle [16] and needle hub [76] placed into half of the safety cover [30] of FIG. 6, the needle [16] and needle hub [76], in the first position with the syringe [45] attached to the needle hub [76].

The needle [16] and needle hub [76] are depicted into half of the safety cover [30], the needle [16] and needle hub [76] in the initial position, with the syringe [45] attached to the needle hub [76]. The syringe volume scale [46] need not be placed in this position because it can be rotated later, on the needle hub [76], so that the scale [46] is visible through the magnifier [44].

To initiate operation, the syringe [45] is pushed firmly into the needle hub [76] taking care not to depress the flex arms [77].

Figure 13:
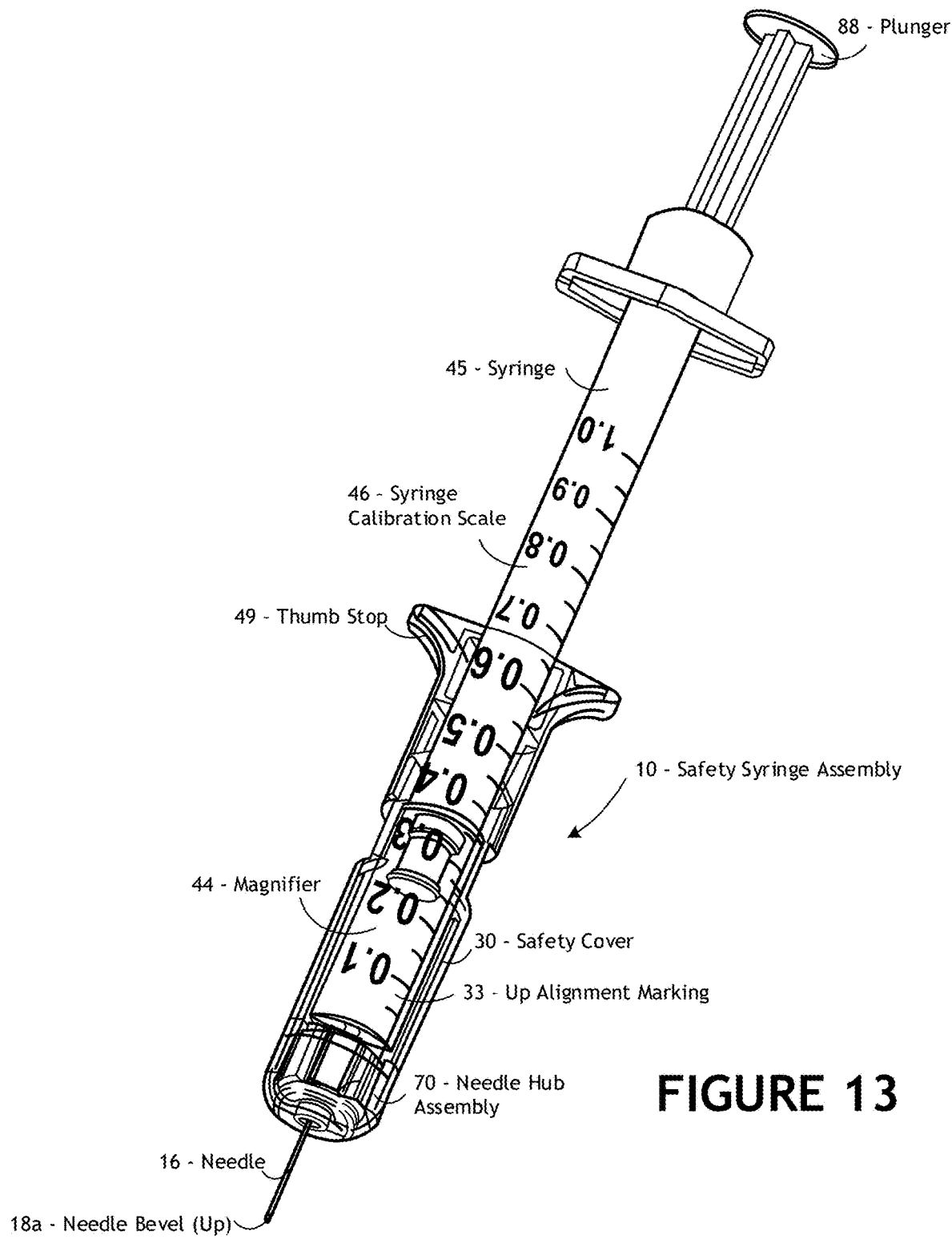
FIG. 13 depicts the safety cover assembly of FIGS. 1A, 1B, and 1C and a syringe in a position that enables for filling of the device from the vial of medical fluid. The safety cover magnifies the volume scale to ensure that the proper amount of fluid is drawn.

FIG. 13 depicts the safety cover [30] assembly of FIGS. 1A, 1B, and 1C and a syringe [45] in position that enables filling of the device from the vial of medical fluid. The safety cover [30] magnifies the volume scale [46] to ensure that the proper amount of fluid is drawn.

The safety cover [30] includes magnification to magnify the volume scale [46] on the syringe [45], for both a long and short needle, and magnifies a large portion of the volume scale [46]. Magnifying is particularly important when injecting low doses (0.01 to 0.30 ml) and permitting the practitioner, nurse, or user to detect air bubbles that can significantly alter the amount of allergen drawn into the syringe [45] and can also increase the risk of blood clots developing in the patient after injection. In addition, magnification can significantly affect the reproducibility of the skin test wheal (bleb) when comparing the saline negative control injection to the actual allergy injection. Proper intradermal allergy testing requires inserting the needle [16] under skin is bevel up [18a] and rotating the needle [16] 180 degrees and injecting the allergen is bevel down [18b] to prevent splashback on the practitioner, nurse, or user if the needle bevel is not fully inserted and to have all of the allergy tests injected needle]16] is bevel down [18b] so every test is done the same way by all practitioners.

For scale alignment, when the thumb stop [49] and the plunger [88] are aligned, the scale [46] appears in the magnifying window and the needle [16] is bevel up [18a].

The safety cover magnifier [44] enlarges the volume scale [46] to ensure that the proper amount of fluid is either drawn or inserted through the syringe [45]. With the needles and syringes, used today, it is difficult to read the small graduations, on the syringe volume scale [46]. Without drawing in the proper amount of allergy fluid, false positives or false negatives are possible, during testing. For example, if the proper volume of allergy fluid is not being drawn into the syringe [45], allergy testing may be less affective.

Also depicted is the needle hub indexing flat toward the magnifier. This embodiment ensures that the needle [16] is always pointed upward toward the up-alignment marker [33], is always 90 degrees from the needle hub flat and that the needle, the needle bevel, the needle hub are always indexed, with respect to the safety cover [30], enabling the needle bevel to be pointed toward the up-alignment marker [33], when viewed through the magnifier [44] or gives the user knowledge of the position of the needle bevel position relative on the safety cover.

To perform a visual check, the needle [16] should be clearly visible in the magnifier [44] of the safety cover with the needle bevel [18] facing toward the red stripe.

To initiate filling, the one or more flex arms [77] are pressed, and the safety cover [30] slides back on the syringe [45] to expose the needle [16]. Then, the safety syringe assembly [10] is filled to the desired level, as the safety cover [30] is unlocked into this position, as the syringe [45] is held and the plunger [88] is pulled to fill.

To dispose after use, the plunger [88] is pulled back so that the needle hub assembly [70] is in the shipping position and the arms [77] are again depressed, continuing pulling until the needle hub assembly [70] snaps into the disposal pockets [32] and the syringe [45] pops off.

The release points on the needle hub [76] are tapered such that after injection, the safety cover [30] can be moved into a locked position that insures that the needle [16] with allergy fluid, potential blood and bodily fluid will not expose the medical professional to any bio-hazards because the safety cover [30] will completely cover the needle [16].

The safety cover [30], with the needle [16] and needle hub [76] in the locked position lock the safety cover [30], needle [16] and needle hub [76] together such that this bio-hazard can be properly disposed of, in a sharps container and the syringe [45] can be separated from the safety cover [30], needle [16] and needle hub [76] for recycling by placing the syringe [45] in a separate container.

Figure 14A:
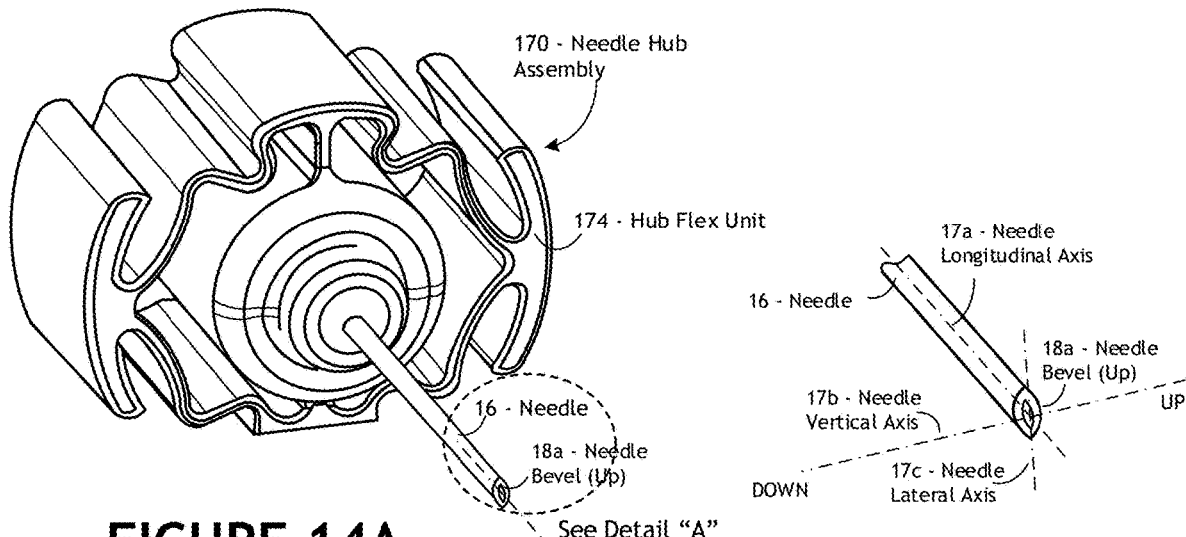
FIG. 14A depicts a front view and FIG. 14B depicts a rear view of another preferred embodiment of the needle hub assembly of FIGS. 1A, 1B, and 1C, including the needle, a needle hub, and a needle flex unit. Detail "A" is an exploded view showing needle orientation and alignment.
Figure 14B:
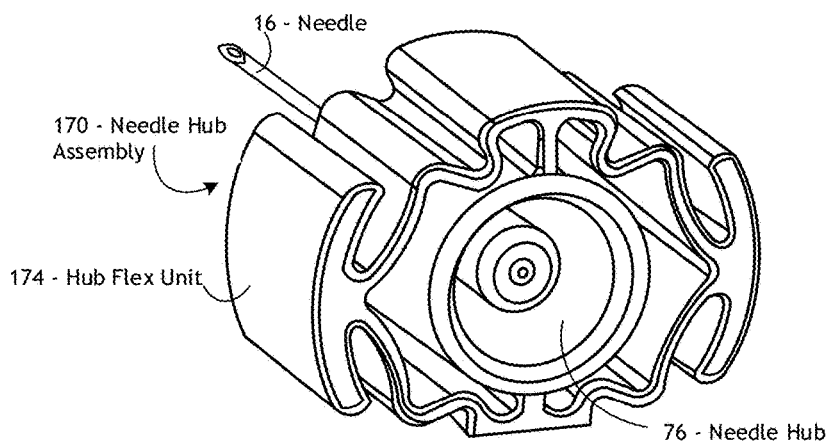

FIG. 14A depicts a front view and FIG. 14B depicts a rear view of a second preferred embodiment of the needle hub assembly [170] of the safety syringe assembly depicted in FIGS. 1A, 1B, and 1C, including the needle [16], a needle hub [76], and a needle flex unit [174]. The needle hub assembly [170] includes locking pads and four spring members, two spring members for each pad, that are used to hold the needle [16] and needle hub [76] in an initial position and are used to lock the needle [16] and needle hub [76] in a locked position for disposal.

The needle, as depicted in FIGS. 14A and 14B and further shown in Detail "A" includes a longitudinal axis [17a], a vertical axis [17b], and a lateral axis [17c]. Preferably, the top of the needle bevel is aligned with the vertical axis [17b] as shown in DETAIL "A" when the needle bevel is pointed upward.

Preferably, the needle is initially positioned horizontally with the bevel facing upward. In the real world, the medical professional using the syringe assembly will not be using a leveler and the needle will not be lying on a horizontal plane. Accordingly, the initial position will be horizontal with the bevel facing upward, 75 degrees about the vertical axis [17b].

Once the needle is under the skin of the patient [66], the needle [16] is inverted from a bevel-up position [18a] to a bevel-down position [18b] to avoid splash-back or other contamination to the medical professional.

FIG. 15 depicts still another embodiment of the safety syringe assembly [210] for use in the processes of the present invention. A lock lever [212] enables unobstructed movement of the needle hub [276] from the insertion position to the disposal position along with a Detail "B" depicting an exploded view of the lock lever [212]. The lock lever [212] ensures that the needle hub [276] will not become reengaged with the safety cover window [239] of the safety cover [230].

FIG. 16 depicts yet another embodiment of a safety syringe assembly [310] for use in the processes of the present invention. A syringe [345] is secured to a needle hub [376] which securely retains a needle [16] having a needle bevel positioned upward [18a] prior to insertion. A lock lever [312] is depicted which enables movement of the needle hub [376] from the insertion position to the disposal position along with a Detail "C" of the lock lever [312]. The lock lever [312] ensures that the flex arm [77] of the needle hub [376] will not become reengaged with the window [339] of the safety cover [330].

Figure 17A:
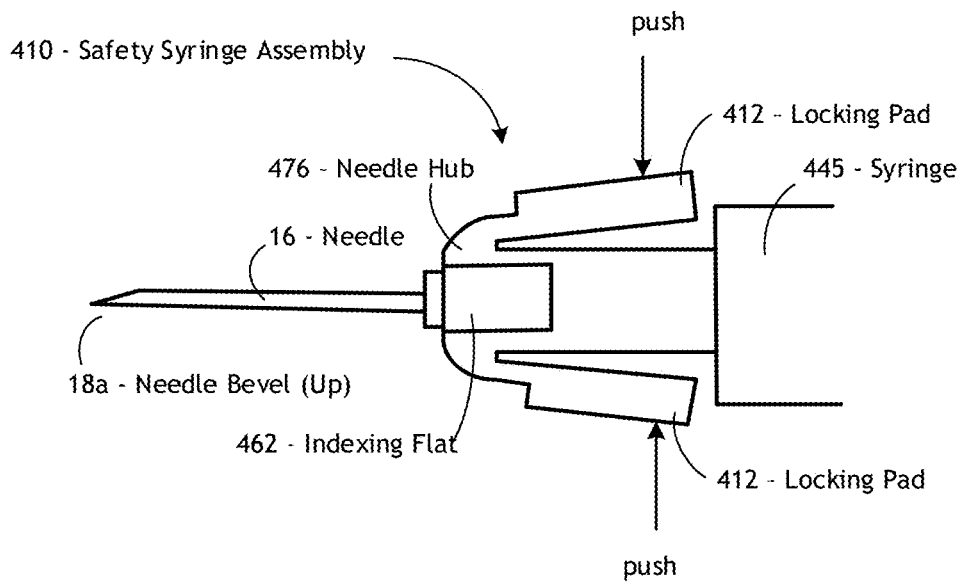
FIG. 17A depicts a side view of still yet another preferred embodiment of a safety syringe assembly for use in the processes of the present invention, with push locking pads and an indexing flat.
Figure 17B:
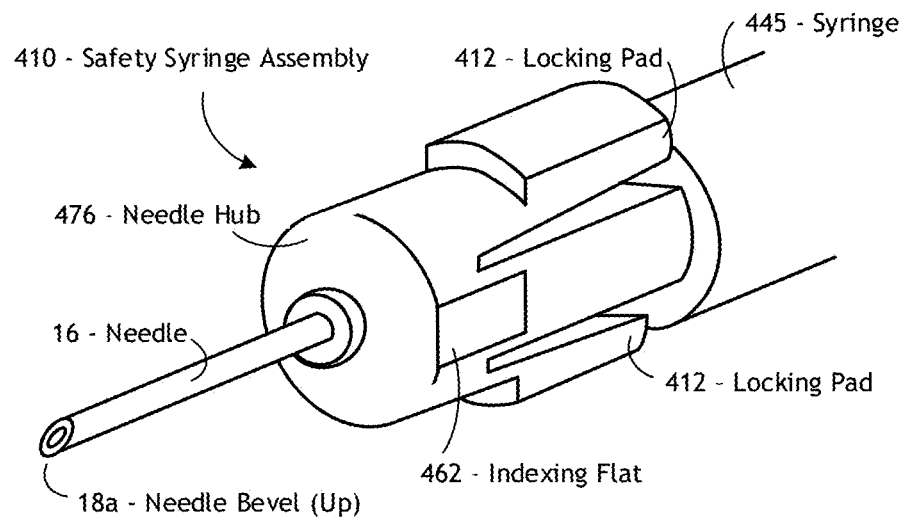
FIG. 17B depicts a front elevational view of the safety syringe assembly of FIG. 17A.

FIGS. 17A and 17B depict still yet another embodiment of a safety syringe assembly [410] for use in the processes of the present invention. A syringe [445] is secured to a needle hub [476] which retains a needle [16] having a needle bevel positioned upward [18a] prior to insertion. A pair of opposing push locking pads [412] and an indexing flat [462] positioned on the needle hub [476] between the pair of opposed locking pads [412].

The pair push locking pads [412] are used when the needle hub [476] moves through the safety cover from the shipping position to the injection position or from the injection position to the disposal position.

The teachings of the needle hub assemblies depicted in FIGS. 7A and 7B, and 14A and 14B may be used in the safety syringe assemblies depicted in FIGS. 15 and 16 along with only minor modifications to the safety cover [30]. Also, hub units that do not flex may also be used in FIGS. 15, 16, and 17.

In addition, one skilled in the art will readily recognize that the safety cover [30] may also be deployed in a broad range of safety syringe assemblies.

For shipping, the hub with flex arms [77] is positioned in the safety cover windows [39] with the needle [16] pointing toward the sharps guard and the needle bevel [18] toward the red stripe.

The syringe [45] can be rotated to any position, but the needle bevel [18] will maintain its position.

The safety syringe assembly [10] is snapped off and disposed of in recycling. The needle hub assembly [70] is locked into the dispose pocket [32] and cannot be dislodged easily. The needle [16] is contained and is disposed of in the sharps container while the syringe [45] is recycled.

Throughout this application, various Patents and Applications are referenced by number and inventor. The disclosures of these documents in their entireties are hereby incorporated by reference into this specification to more fully describe the state of the art to which this invention pertains.

It is evident that many alternatives, modifications, and variations for processes for utilizing the safety syringe assemblies of the present invention will be apparent to those skilled in the art in lieu of the disclosure herein. It is intended that the metes and bounds of the present invention be determined by the appended claims rather than by the language of the above specification, and that all such alternatives, modifications, and variations which form a conjointly cooperative equivalent are intended to be included within the spirit and scope of these claims.

PARTS LIST

10. Safety Syringe Assembly—1st Preferred Embodiment
16. Needle
17a. Needle Longitudinal Axis
17b. Needle Vertical Axis
17c. Needle Lateral Axis
18a. Needle Bevel (Up)
18b. Needle Bevel (Down)
30. Safety Cover
32. Disposal Pocket
33. Up Alignment Marker
34. Down Alignment Marker
36. Safety Cover First Portion
38. Safety Cover Second Portion
39. Safety Cover Window
40. Breakaway Cap
44. Magnifier
45. Syringe
46. Syringe Calibration Scale
49. Thumb Stop
62. Indexing Flat
64. Indexing Ramp
66. Skin of Patient
70. Needle Hub Assembly
74. Hub Flex Unit
76. Needle Hub
77. Hub Flex Arm
78. Hub Flat
82. Alignment Pins
84. Alignment Holes
86. Hub Well
88. Plunger 110. Safety Syringe Assembly—2$^{nd}$ Preferred Embodiment
  170. Needle Hub Assembly
  174. Hub Flex Unit
210. Safety Syringe Assembly—3$^{rd}$ Preferred Embodiment
  212. Lock Lever
  230. Safety Cover
  239. Safety Cover Window
  245. Syringe
  270. Needle Hub Assembly
  276. Needle Hub
310. Safety Syringe Assembly—4$^{th}$ Preferred Embodiment
  312. Lock Lever
  329. Safety Cover Window
  330. Safety Cover
  345. Syringe
  376. Needle Hub
410. Safety Syringe Assembly—5$^{th}$ Preferred Embodiment
  412. Locking Pad
  445. Syringe
  462. Indexing Flat
  476. Needle Hub

The invention claimed is:

1. A method for inserting fluid under skin of a patient providing one-handed operation for allergy testing, said method comprising:
  initially locating a first alignment marking on a safety syringe assembly, said safety syringe assembly including a needle hub securely retaining a needle, said needle having a needle bevel;
  using said first alignment marking to position said needle for insertion under said skin of said patient with said needle bevel pointed upward;
  inserting said needle bevel under said skin of said patient;
  subsequently rotating said safety syringe assembly after said needle bevel has been inserted under said skin of said patient to a bevel pointed downward position; and
  inserting said fluid through said needle into said patient, said first alignment marking providing identification of orientation of said needle bevel while said needle bevel is under said skin of said patient and cannot be seen.

2. The method for inserting fluid under skin of a patient providing one-handed operation for allergy testing of claim 1, wherein said [method is used in allergy testing and said first alignment marking is color coded indicating said needle bevel is pointed upward] safety syringe assembly includes a safety cover, a portion of said safety cover being made of a clear material so that light can pass therethrough, said portion including magnification such that a dosage calibration scale, said needle bevel, and air bubbles are viewable.

3. The method for inserting fluid under skin of a patient providing one-handed operation for allergy testing of claim 1, wherein said first alignment marking facilitating positioning of an injection angle for insertion of said needle bevel under said skin of said patient.

4. The method for inserting fluid under skin of a patient providing one-handed operation for allergy testing of claim 1, wherein said first alignment marking facilitates positioning depth of said needle bevel under said skin of said patient.

5. The method for inserting fluid under skin of a patient providing one-handed operation for allergy testing of claim 1, wherein insertion of said fluid occurs in said bevel pointed downward position under said skin of said patient such that a back splash is retained under said skin of said patient.

6. The method for inserting fluid under skin of a patient providing one-handed operation for allergy testing of claim 1, further comprising said needle hub being disposed within a needle hub assembly that is securely positionable within a safety cover in a shipping position prior to needle insertion, said needle hub assembly being securely positionable within said safety cover during needle insertion, said needle hub assembly being securely positionable within said safety cover in a disposal position after said needle has been used.

7. The method for inserting fluid under skin of a patient providing one-handed operation for allergy testing of claim 1, further comprising said needle hub being a needle hub assembly including a hub flex unit having a first diameter in a shipping position, a second diameter in an insertion position, and a third diameter in a disposal position.

8. A method for inserting fluid under skin of a patient providing one-handed operation for allergy testing, said method comprising:
  providing a safety syringe assembly having a safety cover and a needle hub, a needle being mountable on said needle hub, said needle having a needle bevel, said needle hub being securely disposed within said safety cover; and
  providing a first alignment marking on said safety syringe assembly, said first alignment marking indicating orientation of said needle bevel for insertion of said needle into said skin of said patient with said needle bevel pointed upward, said first alignment marking indicating orientation of said needle bevel for subsequent rotation of said needle bevel such that said fluid can be inserted through said needle in a bevel pointed downward position after insertion such that a splash back from said safety syringe assembly remains under said skin of said patient, said first alignment marking indicating orientation of said needle bevel while said needle bevel is under said skin of said patient and cannot be seen.

9. The method for inserting fluid under skin of a patient providing one-handed operation for allergy testing of claim 8, wherein said first alignment marking facilitating positioning of an injection angle for insertion of said needle bevel under said skin of said patient.

10. The method for inserting fluid under skin of a patient providing one-handed operation for allergy testing of claim 8, wherein said first alignment marking facilitates positioning depth of said needle under said skin of said patient.

11. The method for inserting fluid under skin of a patient providing one-handed operation for allergy testing of claim 8, wherein said first alignment marking is color coded having a first color for a needle bevel upward position and a second color indicating said needle bevel is in a pointed downward position.

12. The method for inserting fluid under skin of a patient providing one-handed operation for allergy testing of claim 8, further comprising said needle hub being disposed within a needle hub assembly that is securely positionable within a safety cover in a shipping position prior to needle insertion, said needle hub assembly being securely positionable within said safety cover during needle insertion, said needle hub assembly being securely positionable within said safety cover in a disposal position after said needle has been used.

13. The method for inserting fluid under skin of a patient providing one-handed operation for allergy testing of claim 8, further comprising said needle hub being a needle hub assembly including a hub flex unit having a first diameter in a shipping position, a second diameter in an insertion position, and a third diameter in a disposal position.

14. The method for inserting fluid under skin of a patient providing one-handed operation for allergy testing of claim 1, wherein said safety syringe assembly includes a safety cover, a portion of said safety cover being made of a clear material so that light can pass therethrough, said portion including magnification such that a dosage calibration scale, said needle bevel, and air bubbles are viewable.

15. The method for inserting fluid under skin of a patient providing one-handed operation for allergy testing of claim 8, wherein said safety syringe assembly includes a safety cover, a portion of said safety cover being made of a clear material so that light can pass therethrough, said portion including magnification such that a dosage calibration scale, said needle bevel, and air bubbles are viewable.

* * * * *